United States Patent [19]
Harrisberger

[11] 3,934,455
[45] Jan. 27, 1976

[54] APPARATUS FOR TESTING A SAND SAMPLE

[75] Inventor: William H. Harrisberger, Tulsa, Okla.

[73] Assignee: The Dow Chemical Company, Midland, Mich.

[22] Filed: Feb. 13, 1974

[21] Appl. No.: 442,283

[52] U.S. Cl. ................................. 73/38; 23/230 EP
[51] Int. Cl.² ............................................... G01N 15/08
[58] Field of Search ................. 73/38, 94; 23/230 EP

[56] References Cited
UNITED STATES PATENTS

| | | | |
|---|---|---|---|
| 1,368,147 | 2/1921 | Henneböhle | 73/94 |
| 2,705,418 | 4/1955 | Reichertz et al. | 73/38 |
| 3,139,747 | 7/1964 | Ferrell et al. | 73/38 |
| 3,353,407 | 11/1967 | Dietert et al. | 73/94 X |
| 3,608,367 | 9/1971 | Karol | 73/94 |

FOREIGN PATENTS OR APPLICATIONS

| | | | |
|---|---|---|---|
| 179,713 | 6/1966 | U.S.S.R. | 73/38 |

Primary Examiner—Richard C. Queisser
Assistant Examiner—John S. Appleman
Attorney, Agent, or Firm—V. Dean Clausen; Lloyd S. Jowanovitz

[57] ABSTRACT

The apparatus disclosed herein is useful for testing unconsolidated sand samples from oil-bearing or gas-bearing earth formations. Basically, the device comprises a cylinder equipped with opposing pistons. The sand sample is placed in the cylinder between the pistons and then compacted by moving the pistons toward each other. The force for moving the pistons is supplied by a fluid, such as air or hydraulic oil, which is injected under pressure into a chamber defined in the cylinder behind each piston. The compacted sample is then subjected to various test procedures involving permeability measurements, consolidation tests, and flow studies.

1 Claim, 2 Drawing Figures

APPARATUS FOR TESTING A SAND SAMPLE

BACKGROUND OF THE INVENTION

This invention relates broadly to procedures for effecting sand control in a sub-surface earth formation. More specifically, the invention concerns an apparatus useful for testing a sample of unconsolidated sand for the purpose of simulating actual consolidation of the sand body in the formation.

One of the problems encountered in obtaining oil or gas from a subsurface earth formation is unconsolidated sand, which can be carried into the well bore along with the oil or gas. The problem can be alleviated by treating the formation sand with various chemicals to consolidate the sand particles. Before actual consolidation treatment is begun, a sample of the unconsolidated sand is tested for fluid permeability and other characteristics. The sample is then treated with the appropriate chemicals under simulated formation conditions.

A common procedure for the simulated test involves placing a container, such as a metal cylinder which is closed at one end, on a vibrating table. With the table vibrating, 100cc of water (approximately 35% of capacity) is placed in the cylinder, and the unconsolidated sand is sifted into the cylinder until it is full of moist, compacted sand. The open end of the cylinder is then capped and the sample is checked for fluid permeability, using a light oil at residual water saturation. The sand sample is then treated to consolidate the particles and the permeability of the sample to diesel oil is determined.

The prior test procedure has several disadvantages. One drawback is that many of the unconsolidated soils to be tested contain high concentrations of silt, clay, or other non-sand fractions. When sand of this type is packed into the test container, the difference in texture of the sand and non-sand fractions causes a segregation within the sample. The result is that a uniform, isotropic sand pack cannot be obtained. In a sand pack of a non-uniform character, it is difficult to obtain an accurate flow profile in checking the sample for fluid permeability. Also, the sand pack will have low fluid permeability, which would require high injection pressures. When a treating fluid is forced through a low permeability sample, therefore, such as a sample containing non-sand fractions, the high pressure required to force the fluid through the sand pack will disturb the pack. This disturbance will alter the flow profile of the pack and thus result in incomplete coverage of the compacted sample by the treating fluids.

Another disadvantage of the vibration technique is that the amount of compaction which can be imparted to each sample is not always reproducible from one test to another. For example, reproducibility of compaction for sand which is clean of silt and clay is good. In a sand sample which contains silt and clay fractions (dirty sands), however, the compaction reproducibility is very poor. In fact, the compaction reproducibility becomes worse as the sand becomes dirtier. Since this test also requires compaction reproducibility for dirty sands, in order to get an accurate flow profile in the compacted sample, the objective was to find a way to solve the problem. The sampling apparatus of this invention achieves this objective.

Another reason which makes it difficult to obtain a uniform sand pack using the prior procedure is a natural occurrence known as the arching principle. An illustration of the arching principle is that when particulate matter, such as sand, is placed in a cylindrical vessel the particle mass will arch itself to the walls of the container if the ratio of the container diameter to the length is more than 1 to 1. As a specific example, if the ratio is about 1 to 3, or higher, several arched areas will be present in the compacted sample. Where the sample has distinct arched areas therefore, the porosity of the sample will vary enough so that there is a definite non-uniformity in the sand pack.

SUMMARY OF THE INVENTION

The apparatus of this invention is useful for testing a sand sample from a subsurface earth formation. The apparatus includes a closed vessel having a first and second piston means, which are slidable toward each other within the vessel. Between the first and second piston means a sample space is defined within the vessel, which is adapted to contain a body of sand. A pressure chamber is defined within the vessel behind each piston.

A conduit in communication with the pressure chambers provides means for carrying a fluid under pressure into the pressure chambers. In operation, the fluid under pressure moves the piston means toward each other to compress the sand body. A second conduit communicates with the sample space. During the test procedure a liquid material is directed into the compressed sand body and then carried from the sand body through the second conduit.

DESCRIPTION OF A PREFERRED EMBODIMENT

Figure 1:
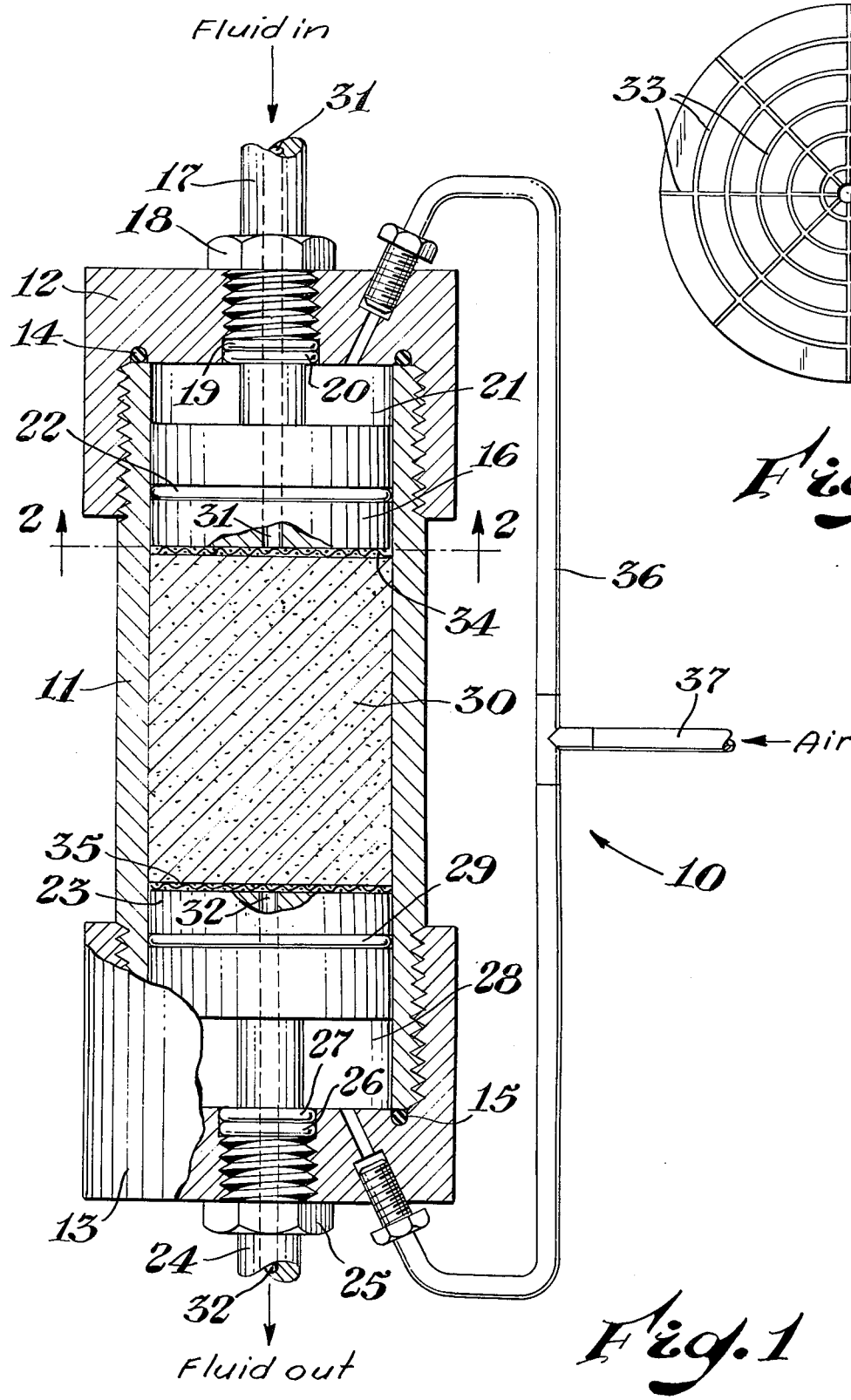
FIG. 1 is a vertical elevation view, mostly in section, of one embodiment of the test apparatus of this invention.

Referring to the drawing, the test apparatus of this invention is indicated generally by the numeral 10. Apparatus 10 comprises basically a closed vessel, as defined by a cylindrical section 11. The cylinder section 11 includes a cap closure 12 at the upper end and a similar cap closure 13 at the lower end. Preferably, the closures 12 and 13 are screw-on caps. However, any type of closure which will provide an air-tight seal on the cylinder section 11 may be used.

An O-ring 14 enhances the sealing of cap 12 to the upper edge of cylinder 11. Similarly, an O-ring 15 assures sealing contact of cap 13 to the lower edge of cylinder 11. Installed in the upper part of cylinder 11 is a slidable piston which comprises a piston head 16 and piston rod 17. The piston rod 17 extends from the piston head 16 upwardly through cap 12. In cap 12 the piston rod 17 is held in place by a threaded follower plug 18.

Follower plug 18 seats down against a metal ring 19 and an O-ring 20. The rings 19 and 20 provide an additional means for sealing of vessel 11 against air leakage. Within vessel 11 a pressure chamber 21 is defined between the rear edge of piston head 16 and the inner wall surface of cap 12. Additional means for sealing the vessel 11, so that pressure chamber 21 can receive and hold a fluid under pressure, is provided by an O-ring 22 on piston head 16.

A second slidable piston, comprising piston head 23 and piston rod 24, is installed in the lower part of the vessel 11. From the piston head 23, the piston rod 24 extends downwardly through cap closure 13. In cap 13 the rod 24 is held in place by a follower plug 25. The follower plug 25, which is similar to follower plug 18, seats down against a metal ring 26 and an O-ring 27.

A second pressure chamber 28 is defined between the rear edge of piston head 23 and the inner wall surface of cap 13. Additional seal means for the pressure chamber 28 is provided by an O-ring 29 on the piston head 23. When the piston heads 16 and 23 are in operating position in vessel 11, a space is defined between the respective front faces of each piston head. The purpose of this space is to contain a body of unconsolidated sand 30, as indicated in the drawing.

As explained later in this text the sand body 30 is compacted between the piston heads for testing purposes. An inlet passageway 31 extends centrally through the piston rod 17 and piston head 16. Passageway 31 provides a means for directing a liquid material into the sand body 30. Means for carrying the liquid out of sand body 30 are provided by a similar passageway, which is an outlet passageway, as indicated at 32. Passageway 32 extends centrally through the piston head 23 and piston rod 24.

Figure 2:
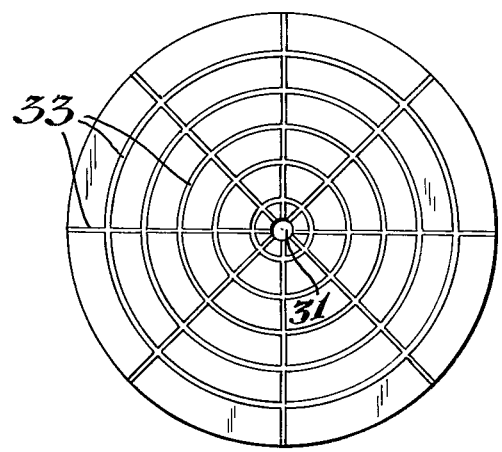
FIG. 2 is a cross section view, taken on line 2—2, which illustrates the distributor channels in the front face of a piston head in the test apparatus of FIG. 1.

The view of FIG. 2 illustrates the front face of piston head 16. As shown, the front face of this piston head includes a series of shallow, interconnected channels 33. The channels 33, which form a spider web network, aid the distribution of the liquid into sand body 30. The front face of piston head 23 includes a similar set of channels (not shown), which help to drain the liquid from the sand body 30 into the outlet passageway 32.

In vessel 11 a screen 34 is fitted between the front face of piston head 16 and the sand body 30. A similar screen 35 is sandwiched between the front face of piston head 23 and sand body 30. The function of the screens 34 and 35 is to prevent the sand particles from plugging the liquid-carrying channels in the front faces of piston heads 16 and 23 when the sample is compacted.

One end of a tube conduit 36 connects into the pressure chamber 21 through an appropriate fitting and an opening into the chamber 21. The opposite end of conduit 36 connects into the pressure chamber 28 by a similar arrangement. Conduit 36, in turn, connects into a fluid source (not shown) through a branch line 37. Conduit 36 thus provides means of carrying a fluid into the pressure chambers 21 and 28, for moving the piston heads 16 and 23 within vessel 11.

To illustrate the practice of this invention, a typical operation for testing an unconsolidated sand sample will now be described. First, a sample of unconsolidated sand from a subsurface earth formation is obtained. The sand body 30 is poured into the vessel 11 and confined between the piston heads 16 and 23. In one embodiment of the invention, air under a positive pressure is directed into the pressure chambers 21 and 28 through conduit 36, to move the piston heads 16 and 23, and thus compress the sample.

In another embodiment, a liquid, such as hydraulic oil, can be injected into the pressure chambers 21 and 28 under high pressure, to move the piston heads, 16 and 23. In this arrangement, the hydraulic oil is the pressure fluid instead of air. Where oil is used as the pressure fluid, the caps 12 and 13 are provided with bleed valves to vent the air out of the pressure chambers as the oil is pumped in. This modification to the apparatus is not illustrated herein in order to simplify the drawing.

The sample is compacted sufficiently so that the unconsolidated sand has about the same density as it had in the earth formation. The next step is to determine flow permeability of the compacted sample. This is done by directing a fluid into the sand body 30 through the inlet passageway 31. In general, the fluid should be one which is chemically inert to the sand particles. Typical fluids which may be used are diesel oil, kerosene, and liquids of this type. The flow permeability is determined by computing the rate at which the particular fluid used will flow through the compacted sample at a given pressure.

The next phase is a simulated formation conditioning step. The first step here is to flush the sand body 30 with a scavenger material, such as a mud acid. The mud acid flush is directed through passageway 31 to dissolve the non-sand fractions, such as silt and clay, in the sand body 30. The purpose is to prepare the sand grains for accepting a treating fluid. The next step is to run an alcohol drying agent through the sand body 30 to dissolve the mud acid and pick up water trapped in the sand sample. Following this step, the sand body 30 is flushed with a liquid which will pick up the alcohol, such as a diesel oil.

The next phase involves the actual consolidation of the sand grains. In this procedure a liquid resin material is directed into the sand body 30 through passageway 31 to adhere the sand particles together. Suitable resins are those materials known to the art which are typically employed in sand consolidation operations. The next step is to flush the sample with an oil which is immiscible with the resin. The purpose of this flush is to remove the resin material which becomes trapped in the pore space between the agglomerated sand grains.

The next step in the consolidation phase is to cure the resin material in sand body 30. This is done by immersing the closed vessel 11 containing the compacted sand body 30 in a hot water or hot oil bath. During the curing step the temperature of the bath is held within a range which approximates actual formation temperature conditions. This range will usually be from about 150°F. to 180°F.

After the resin curing step, the vessel 11 is removed from the hot bath to check the inlet passageway 31 and outlet passageway 32 for flow restriction. For example, when the resin is fed through the passageways 31 and 32 the material will sometimes deposit in these passageways and harden during the curing step. The result is a restriction which impedes fluid flow through the passageways. The next step is a final permeability test. For checking final permeability, the test is conducted in the same manner as the initial permeability test described above.

The last step is a test to determine the strength of the compacted sand body under unconfined conditions. This is done by drilling out a small diameter core from each end of the compacted sample and then inserting the cores, one at a time, in a Tinius Olsen testing machine. Each core sample is then compressed in the machine to the point at which it crumbles. The strength reading of the core is taken at this point. The fluid flow readings obtained in the final permeability test are compared with those recorded for the initial test. A comparison of the readings is then made to determine whether the altered permeability which results from sand consolidation is within acceptable limits.

The test apparatus of this invention has several advantages over the prior apparatus. A major advantage is that the present test vessel can accommodate a larger sand sample than the prior apparatus without encountering the problem of the arching principle described above. To illustrate, assume that the cylindrical vessel 11 has an inside diameter of 2 inches, an overall length of 6 inches, and the opposing piston heads 16 and 23 are each 2 inches in diameter. As installed in vessel 11, the opposing pistons are positioned so that when each piston reaches the end of its stroke the space between the piston heads 16 and 23 will not exceed 4 inches.

In other words, the maximum compacted length for the sample 30 will be the 4-inch space between the piston heads. Although the sample length is twice the distance of the vessel diameter (2 inches) the arching rule is not violated in that each piston will compact half (approximately 2 inches) of the total sample. Another advantage of the present apparatus is that the sand sample can be loaded into the vessel 11 and compacted without having to first clean the sample to remove non-sand fractions, such as oil, water, silt and clay. Another advantage is the use of mechanical force, such as fluid pressure, to achieve compaction of the sample. This permits the flow profile for low permeability soils to be uniform throughout the sample. Another advantage is that the compaction applied to the sample is reproducible and it can be varied to accommodate soils of different textures.

The invention claimed is:

1. A method for testing a sand sample from a subsurface earth formation, which comprises the steps of:
    placing an unconsolidated sand sample in a rigid, closed cylindrical vessel;
    compacting the unconsolidated sand sample within the vessel to obtain a uniform pack by compressing the sample between a first piston and a second piston, the pistons being slidable toward each other within the vessel; and the diameter of the vessel, as related to the length of the sand sample, being a ratio of not more than 1 to 2;
    passing a first fluid through the compacted unconsolidated sand sample to determine flow permeability of the unconsolidated sand sample;
    passing a second and third fluids through the compacted, unconsolidated sand sample to condition the sand particles for accepting a fourth fluid which defines a consolidating fluid;
    directing the consolidating fluid into the sand sample to adhere the sand particles together, to thereby consolidate the sand sample;
    flushing the consolidated sand sample with a fifth fluid to remove consolidating fluid which is trapped in pore spaces between the sand particles;
    curing the consolidating fluid by heating the vessel to a temperature sufficient to cure the said consolidating fluid; and
    passing a sixth fluid through the compacted, consolidated sand sample to determine the flow permeability of the said consolidated sample.

* * * * *